US00PP17379P3

(12) United States Plant Patent
Danziger

(10) Patent No.: US PP17,379 P3
(45) Date of Patent: Jan. 23, 2007

(54) **DOUBLE *IMPATIENS* PLANT NAMED 'DANMUORGLOW'**

(50) Latin Name: *Impatiens walleriana*
Varietal Denomination: Danmuorglow

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/138,261

(22) Filed: May 27, 2005

(65) Prior Publication Data

US 2006/0272065 P1 Nov. 30, 2006

(51) Int. Cl.
*A01H 5/00* (2006.01)

(52) U.S. Cl. ..... Plt./317

(58) Field of Classification Search ..... Plt./317
See application file for complete search history.

*Primary Examiner*—Kent Bell
(74) *Attorney, Agent, or Firm*—Foley & Lardner LLP

(57) ABSTRACT

A new and distinct Double *Impatiens* plant named 'Danmuorglow' characterized by having compact and rounded growth habit; double, orange colored flowers; green colored leaves; and good branching.

2 Drawing Sheets

Botanical designation: *Impatiens walleriana.*
Variety denomination: 'Danmuorglow'.

BACKGROUND OF THE INVENTION

The present invention relates to a new and distinct cultivar of Double *Impatiens* plant, botanically known as *Impatiens walleriana*, herein after referred to by the cultivar name 'Danmuorglow'.

The new Double *Impatiens* cultivar is a product of a planned breeding program conducted by the Inventor, Gabriel Danziger, in Moshav Mishmar Hashiva, Israel. The objective of the breeding program is to develop a new Double *Impatiens* variety with compact and rounded, growth habit, orange colored flowers, green colored leaves, and good branching habit.

The new *Impatiens* cultivar originated from a cross made in a controlled breeding program by the Inventor, Gabriel Danziger, in 2003 in Moshav Mishmar Hashiva, Israel. The female or seed parent is the *Impatiens walleriana* cultivar designed '477 HF' (unpatented) and is characterized by having single, orange colored flowers and a compact, growth habit. The male or pollen parent is the *Impatiens walleriana* cultivar designated '326 HF' (unpatented) and is characterized by having semi-double, salmon colored flowers. 'Danmuorglow' was discovered and selected by the Inventor in May of 2003 as a flowering plant within the progeny of the stated cross in a controlled environment in. Moshav Mishmar Hashiva, Israel.

Asexual reproduction of the new cultivar by stem tip cutting was first performed in July of 2003 in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of the new Double *Impatiens* cultivar 'Danmuorglow' which in combination distinguish this Double *Impatiens* as a new and distinct cultivar:

1. Compact and rounded growth habit;
2. Double, orange colored flowers;
3. Green colored leaves; and
4. Good branching.

Plants of the new Double *Impatiens* 'Danmuorglow' differ from plants of the parents, '477 HF' (unpatented) and '326 HF' (unpatented) in the following characteristics described in Table 1:

TABLE 1

| Trait | New Cultivar 'Danmuorglow' | Female Parent '477 HF' (unpatented) | Male Parent '326 HF' (unpatented) |
|---|---|---|---|
| Color of opening petals (upper surface): | Orange-red group, RHS N 30 B | Orange-red group, RHS 32 A | Red group, RHS 52 C |
| Flower Type | Double flower | Single flower | Semi-double flower |
| Leaf size | Length: 4 cm Width: 3 cm | Length: 5 cm Width: 3 cm | Length: 6 cm Width: 3.5 cm |
| Plant height | 12 cm | 15 cm | 18 cm |

Of the many commercial cultivars known to the present Inventor, the most similar in comparision to the new Double *Impatiens* cultivar 'Danmuorglow' is a Double *Impatiens* called 'Fiesta Deep Orange'. In side-by-side comparisons conducted in Moshav Mishmar Hashiva, Israel, plants of 'Fiesta Deep Orange' differed from plants of 'Danmuorglow' primarily in flower color and leaf color as provided in Table 2:

TABLE 2

| Trait | New Cultivar 'Danmuorglow' | Comparison Cultivar 'Fiesta Deep Orange' |
|---|---|---|
| Color of opening petals (upper surface): | Orange-red group RHS N 30B | Orange-red group RHS N 30A |
| Leaf color | Green group RHS 137C | Green group RHS 137A |
| Plant height | 12 cm | 14 cm |

BRIEF DESCRIPTION OF THE DRAWINGS

The accompanying colored photographs illustrate the overall appearance of the new Double *Impatiens* cultivar 'Danmuorglow' showing the colors as true as is reasonably possible with colored reproductions of this type. Colors in the photographs may differ slightly from the color values cited in the detailed botanical description which accurately describe the color of the 'Danmuorglow'.

The first photograph shows a side view perspective of a typical 'Danmuorglow' potted plan at 3 months.

The second photograph shows a close-up view of typical flowers and leaves of 'Danmuorglow' at 3 months.

DETAILED BOTANICAL DESCRIPTION

The new Double *Impatiens* cultivar 'Danmuorglow' has not been observed under all possible environmental conditions. The phenotype of the new cultivar may vary with variations in environment such as temperature, light intensity, and daylength, without any change in the genotype of the plant.

The aforementioned photographs, together with the following observations, measurements and values describe plants of the new Double *Impatiens* cultivar 'Danmuorglow' as grown in a greenhouse in Moshav Mishmar Hashiva, Israel, under conditions which closely resemble those generally used in commercial practice. Plants of 'Danmuorglow' are grown in a greenhouse with day temperatures ranging from 25° C. to 30° C. and night temperatures ranging from 18° C. to 25° C. Plants of 'Danmuorglow' are fertilized up to a level of 100 ppm N, 35 ppm P and 120 ppm K. The age of the plants described is 8 weeks. The photographs and descriptions were taken during the winter when outdoor day temperatures ranged from 15° C. to 25° C. and outdoor night temperatures ranged from 10° C. to 15° C.

Color references are made with The Royal Horticultural Society Colour Chart (R.H.S.), 2001 edition, except where general colors of ordinary significance are used. Color values were taken under daylight conditions at approximately 12 noon in Moshav Mishmar Hashiva, Israel.

Classification:
- *Botanical.*—*Impatiens walleriana.*
- *Commercial.*—Musica Orange Glow.

Parentage:
- *Female or seed parent.*—*Impatiens walleriana* cultivar designated as '477 HF' (unpatented).
- *Male or pollen parent.*—*Impatiens walleriana* cultivar designated as '326 HF' (unpatented).

Propagation:
- *Type.*—Stem tip cutting.
- *Time and temperature to initiate roots.*—Summer: 7 to 10 days at 25° C. Winter: 10 to 15 days at 21° C.
- *Time and temperature to produce a rooted cutting or liner.*—Summer: 15 to 18 days at 25° C. Winter: 18 to 21 days at 21° C.
- *Rooting habit and description.*—Fibrous roots, adventitious roots from cutting base.

Plant:
- *General appearance and form.*—Compact and rounded.
- *Growth and branching habit.*—Very good branching.
- *Growth rate.*—2 months from rooted plant to a finished product in 12 to 13 cm pots.
- *Plant height.*—12 cm.
- *Plant width (spread).*—25 cm.

Lateral branches:
- *Quantity per plant.*—Primary Lateral shoots: About 5. Secondary lateral shoots: About 20.
- *Length.*—10 cm.
- *Diameter.*—0.5 cm.
- *Internode length.*—1.5 cm.
- *Strength.*—Strong, very stable.
- *Texture.*—Smooth.
- *Color.*—Upper surface: Yellow green, RHS 144D. Lower surface: yellow green, RHS 144D.

Foliage:
- *Arrangement.*—Alternate.
- *Overall shape of leaf.*—Ovate.
- *Shape at apex.*—Acute.
- *Shape at base.*—Acute.
- *Length.*—4 cm.
- *Width.*—3 cm.
- *Margin.*—Toothed.
- *Texture.*—Upper surface: Smooth. Lower surface: Smooth.
- *Color of mature (developed) leaf.*—Upper surface: Green, RHS 137 C. Lower surface: Green, RHS 139 D.
- *Color of immature (expanding) leaf.*—Upper surface: Green, RHS 137C. Lower surface: Green, RHS 139D.

Venation:
- *Pattern.*—Midrib with secondary veins. Pinnate,only lower surface.
- *Color.*—Upper surface: Midrib: Yellow Green, RHS 145B. Lower surface: Midrib: Green, RHS 146D. Secondary veins: Green, RHS 146D.

Petiole:
- *Length.*—1 cm.
- *Diameter.*—2 mm.
- *Color.*—Upper surface: Green, RHS 144D. Lower surface: Green, RHS 144D.

Flower description:
- *Flower type and habit.*—Double flowers raised above the foliage.
- *Natural flowering season.*—Flowers at any day length. All year round in a greenhouse environment. Flowering is continuous from spring until fall in an outdoor garden.
- *Flowering response.*—8 weeks after planting of rooted cuttings.
- *Quantity of flowers.*—About 10 flowers and buds per stem.
- *Post production longevity.*—Up to six months.
- *Fragrance (if any).*—None.

Corolla:
- *Form.*—Double.
- *Shape.*—Rosette.

*Length.*—4 cm.
*Width.*—4 cm.
*Depth.*—1.5 mm.
*Color.*—Orangered group, RHS N 30B.

Buds:
*Rate of opening* (*from showing color to fully open flower*).—3 days.
*Length.*—1.5 cm.
*Diameter.*—At Apex: 0.5 cm. At Base: 1 cm.
*Shape.*—Rounded.
*Color.*—Orange-red group: RHS 32D, with no changes between apex and base.

Petals:
*Quantity and arrangement per flower.*—About 30 petals, Arrangement: Imbricate.
*Lateral and base petal length.*—About 2 cm.
*Lateral and base petal width.*—About 2 cm.
*Overall shape.*—Obcordate.
*Shape at apex.*—Blunt.
*Margin.*—Entire.
*Aspect.*—Upward.
*Texture.*—Upper surface: Smooth. Lower surface: Smooth.
*Color of opening petals.*—Upper surface: Orange-red group, RHS N 30B. Lower surface: Red-purple group, RHS 40 D.
*Color of fully opened petals.*—Upper surface: Orange-red group, RHS 30A. Lower surface: red group, RHS:41C.

Sepals:
*Quantity per flower.*—2.
*Length.*—About 2 mm.
*Width.*—About 1 mm.
*Overall shape.*—Oblong.
*Apex shape.*—Rounded.
*Base shape.*—Rounded.
*Margin.*—Entire.
*Color.*—Upper surface: RHS 141D, green group. Lower surface: RHS 143C, green group.

Spur:
*Quantity per flower.*—One.
*Length.*—2.5 cm.
*Diameter.*—At apex: 1 mm. At flower: 2 mm.
*Aspect.*—Spur curvature 40°–45° from peduncle.
*Color of spur.*—Towards base: Yellow-Green, RHS145 C. Towards apex: Yellow-Green, RHS145 A.

Peduncles:
*Appearance and angle.*—Erect 90° from corolla.
*Length.*—2.5 cm.
*Diameter.*—2 mm.
*Texture.*—Smooth.
*Strength.*—Stable, flexible.
*Color.*—Yellow-green group, RHS N144D.

Reproductive organs: Sterile, no reproductive organs.

Disease/pest resistance: No sensitivity was observed under regular growing conditions.

Disease/pest susceptibility: No information is currently available.

Low temperature tolerance: Sensitive to temperatures below 10° C.

I claim:

1. A new and distinct Double *Impatiens* plant named 'Danmuorglow', as illustrated and described herein.

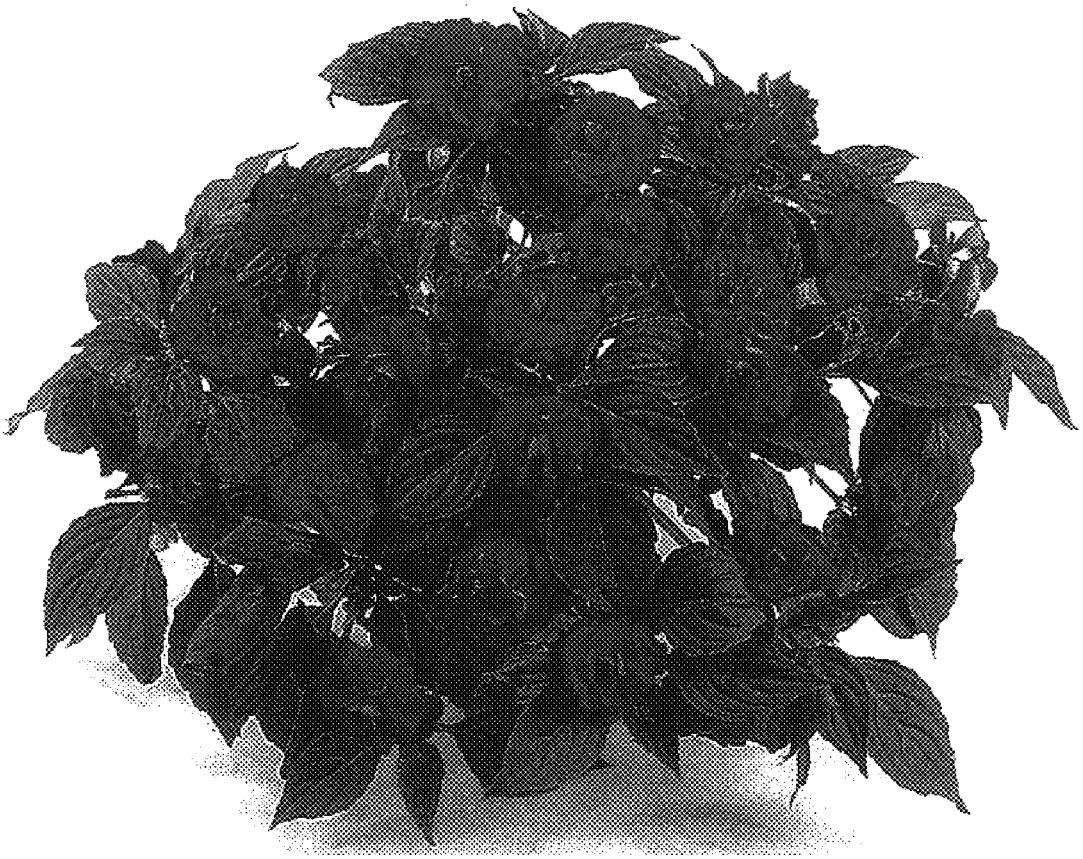

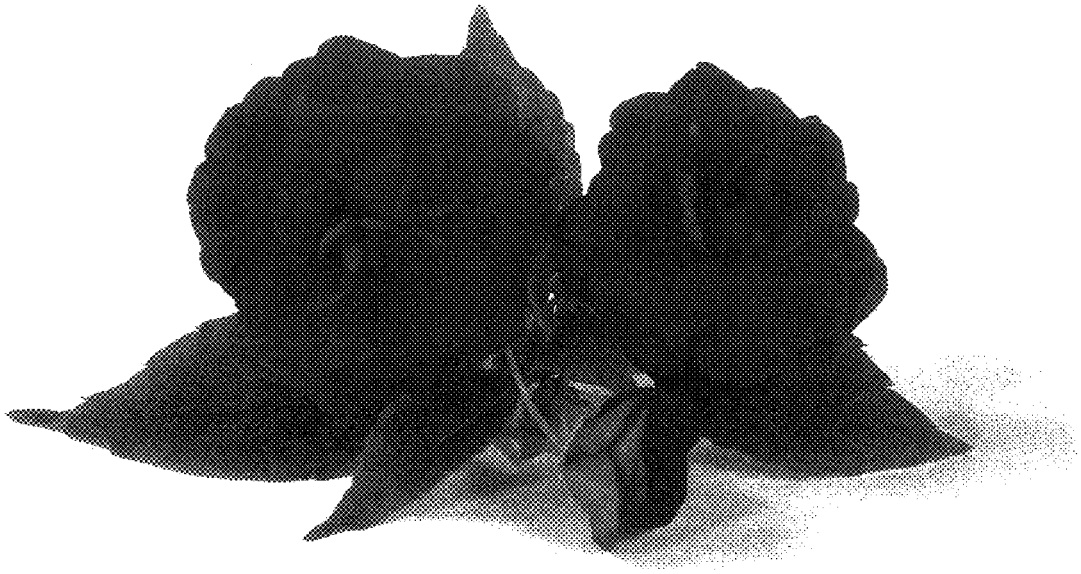

* * * * *